United States Patent [19]

Kanai et al.

[11] Patent Number: 5,104,889

[45] Date of Patent: Apr. 14, 1992

[54] THIAZOLE DERIVATIVES

[75] Inventors: Kenichi Kanai; Kiyoto Goto; Kinji Hashimoto, all of Naruto; Yoshiaki Tsuda, Anan, all of Japan

[73] Assignee: Otsuka Pharmaceutical Factory, Inc., Naruto, Japan

[21] Appl. No.: 529,694

[22] Filed: May 29, 1990

Related U.S. Application Data

[63] Continuation of Ser. No. 196,204, Mar. 28, 1988, abandoned.

[30] Foreign Application Priority Data

Aug. 4, 1986 [JP] Japan .................. 61-183873

[51] Int. Cl.$^5$ .................. C07D 277/42; A61K 31/425
[52] U.S. Cl. ..................... 514/370; 546/209; 548/184; 548/186; 548/191; 548/193; 548/194; 548/203
[58] Field of Search ............ 514/370; 546/209; 548/193, 184, 191, 194

[56] References Cited

U.S. PATENT DOCUMENTS

| 3,192,225 | 6/1965 | Spivack et al. | 260/306.8 |
|---|---|---|---|
| 3,201,409 | 8/1965 | Spivack et al. | 260/306.8 |
| 3,299,087 | 1/1967 | Spivack et al. | 206/306.8 |
| 3,467,666 | 9/1969 | Dexter | 548/193 |
| 4,451,471 | 5/1984 | Ferrini et al. | 424/263 |
| 4,457,936 | 7/1984 | Draeger et al. | 424/270 |
| 4,636,516 | 1/1987 | Kubo et al. | 514/365 |

FOREIGN PATENT DOCUMENTS 0202157 11/1986 European Pat. Off. .
1302433 6/1962 France .
39-5907 4/1964 Japan .

OTHER PUBLICATIONS

Deshpande, R. N. et al., "Aryl 5-Nitro-2-thiazolyl Sulphides, Sulphones and Ethers as Potential Antibacterials", *Journal f. prakt. Chemie*, vol. 316, No. 2 (1974), pp. 349–352.

Primary Examiner—Robert Gerstl
Attorney, Agent, or Firm—Armstrong, Nikaido, Marmelstein, Kubovcik & Murray

[57] ABSTRACT

This invention provides thiazole derivative of the general formula wherein $R^1$, $R^2$, $R^3$, $R^4$, $R^5$ and A are as defined above, and salts thereof. These compounds have particularly potent angiogenesis inhibiting activity.

5 Claims, No Drawings

THIAZOLE DERIVATIVES

This application is a continuation of Ser. No. 196,204, filed Mar. 28, 1988, now abandoned.

TECHNICAL FIELD

This invention relates to novel, pharmacologically active thiazole derivatives and salts thereof.

BACKGROUND ART

The thiazole derivatives of the invention, including salts thereof, are novel compounds not yet described in the literature.

Various N-substituted 2-aminothiazoles more or less relates to the thiazole derivatives of the invention are described in U.S. Pat. Nos.3,192,225, 3,201,409, 3,299,087 and 3,467,666, Laid-open French Patent Specification No.1,302,433 and Laid-open European Patent Specification No.202,157. In these references, however, there is no mentioned made of the thiazole derivatives of the invention, nor is it disclosed that the compounds described in said references have that angiogenesis inhibiting activity to be mentioned later herein which the thiazole derivatives of the invention have.

Accordingly, it is an object of the invention to provide novel thiazole derivatives and salts thereof, which have valuable pharmacological activities, in particular angiogenesis inhibiting activity, as mentioned later herein.

DISCLOSURE OF THE INVENTION

In accordance with the invention, there are provided compounds of the general formula (1) shown below and salts thereof.

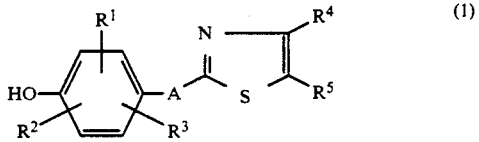

In the above formula, $R^1$ and $R^2$ are the same or different and each is a $C_1$-$C_6$ alkyl group, $R^3$ is a hydrogen atom or a $C_1$-$C_6$ alkyl group, $R^2$ and $R^3$ may combinedly form a —$(CH_2)_4$— group, $R^4$ and $R^5$ are the same or different and each is a hydrogen or halogen atom or a $C_1$-$C_{20}$ alkyl, phenyl, phenylthio, $C_1$-$C_6$ alkylthio or $C_1$-$C_6$ alkylthio-$C_1$-$C_6$ alkyl, nitro, $C_1$-$C_6$ alkoxy-carbonyl-$C_2$-$C_6$ alkenyl, carboxy-$C_2$-$C_6$ alkenyl, carbazoyl, carboxyl, carboxy-$C_1$-$C_6$ alkyl, $C_1$-$C_6$ alkoxy-carbonyl-$C_1$-$C_6$ alkyl, $C_1$-$C_6$ alkoxycarbonyl, piperidinocarbonyl, N,N-di($C_1$-$C_6$ alkyl)aminocarbonyl, N-phenylaminocarbonyl or hydroxy-$C_1$-$C_6$ alkyl group, and A is an imino group, an oxygen or sulfur atom or a sulfinyl, sulfonyl or $C_1$-$C_6$ alkylene group, to the exclusion of the cases where $R^3$ is a hydrogen atom, $R^4$ is a $C_1$-$C_6$ alkyl or phenyl group, $R^5$ is a hydrogen atom and A is an imino group.

The respective groups appearing in the present specification are as follows:

As the $C_1$-$C_6$ alkyl group, there may be mentioned such straight or branched $C_1$-$C_6$ alkyl groups as methyl, ethyl, propyl, isopropyl, butyl, isobutyl, tert-butyl, pentyl and hexyl, among others.

As the $C_1$-$C_{20}$ alkyl groups, there may be mentioned, among others, such $C_1$-$C_{20}$ alkyl groups as heptyl, octyl, nonyl, decyl, undecyl, dodecyl, tridecyl, tetradecyl, pentadecyl, hexadecyl, octadecyl, nonadecyl and eicosyl as well as those $C_1$-$C_6$ alkyl groups mentioned above.

As the $C_1$-$C_6$ alkylthio-$C_1$-$C_6$ alkyl group, there may be mentioned such straight or branched $C_1$-$C_6$ alkylthio-$C_1$-$C_6$ alkyl groups as methylthiomethyl, ethylthiomethyl, 1-propylthiomethyl, isopropylthiomethyl, 1-butylthiomethyl, 2-butylthiomethyl, tert-butylthiomethyl, 1-pentylthiomethyl, 1-hexylthiomethyl, 1-methylthioethyl, 2-methylthioethyl, 2-ethylthioethyl, 3-methylthiopropyl, 2-ethylthiobutyl, 4-methylthiobutyl, 5-methylthiopentyl and 6-methylthiohexyl, among others.

As the $C_1$-$C_6$ alkylthio group, there may be mentioned such straight or branched $C_1$-$C_6$ alkylthio groups as methylthio, ethylthio, 1-propylthio, isopropylthio, 1-butylthio, 2-butylthio, tert-butylthio, 1-pentylthio, 2-pentylthio, 3-pentylthio, 1-hexylthio, 2-hexylthio and 3-hexylthio, among others.

As the halogen atom, there may be mentioned fluorine, chlorine, bromine and iodine.

As the $C_1$-$C_6$ alkoxy moiety of the $C_1$-$C_6$ alkoxycarbonyl, $C_1$-$C_6$ alkoxy-carbonyl-$C_1$-$C_6$ alkyl and $C_1$-$C_6$ alkoxy-carbonyl-$C_2$-$C_6$ alkenyl groups, there may be mentioned such straight or branched $C_1$-$C_6$ alkoxy groups as methoxy, ethoxy, propoxy, isopropoxy, sec-butoxy, tertbutoxy, pentyloxy and hexyloxy, among others.

Examples of the above-mentioned $C_1$-$C_6$ alkoxycarbonyl group are methoxycarbonyl, ethoxycarbonyl, 1-methylethoxycarbonyl, butoxycarbonyl, 1,1-dimethylethoxycarbonyl, pentyloxycarbonyl, hexyloxycarbonyl and the like, examples of the $C_1$-$C_6$ alkoxy-carbonyl-$C_1$-$C_6$ alkyl group are methoxycarbonylmethyl, 2-methoxycarbonylethyl, 3-methoxycarbonylpropyl, 1-methoxycarbonyl-1methylethyl, 4-methoxycarbonylbutyl, 5-methoxycarbonylpentyl, 6-methoxycarbonylhexyl, ethoxycarbonylmethyl, 1-methylethoxycarbonylmethyl, butoxycarbonylmethyl, 2-(1,1-dimethylethoxycarbonyl)ethyl, pentyloxycarbonylmethyl, hexyloxycarbonylmethyl and the like, and examples of the $C_1$-$C_6$ alkoxy-carbonyl-$C_2$-$C_6$ alkenyl group are 1-methoxycarbonylvinyl, 2-methoxycarbonylvinyl, 2-ethoxycarbonylvinyl, 1-(1-methylethoxycarbonyl)vinyl, 2-(1-methylethoxycarbonyl)vinyl, 2-(1-butoxycarbonyl)vinyl, 2-(1-hexyloxycarbonyl)vinyl, 3-methoxycarbonylallyl, 2-methoxycarbonylallyl, 1-methoxycarbonylallyl, 3-ethoxycarbonylallyl, 3-(1,1-dimethylethoxycarbonyl)-1-butenyl, 4-(1-butoxycarbonyl)-1-butenyl, 4-(1-hexyloxycarbonyl)-1-butenyl, 6-methoxycarbonyl-1-hexenyl and the like.

As the carboxy-$C_1$-$C_6$ alkyl group, there may be mentioned such carboxy-$C_1$-$C_6$ alkyl groups as carboxymethyl, 1-carboxyethyl, 2-carboxyethyl, 1-methyl-1-carboxyethyl, 3-carboxypropyl, 4-carboxybutyl, 1,1-dimethyl-2-carboxyethyl, 5-carboxypentyl and 6-carboxyhexyl, among others.

As the carboxy-$C_2$-$C_6$ alkenyl group, there may be mentioned such carboxy-$C_2$-$C_6$ alkenyl groups as 1-carboxyvinyl, 2-carboxyvinyl, 1-carboxyallyl, 2-carboxyallyl, 3-carboxyallyl, 3-carboxy-1-butenyl, 4-carboxy-2-butenyl, 5-carboxy-1-pentenyl and 6-carboxy-3-hexenyl, among others.

As the hydroxy-$C_1$-$C_6$ alkyl group, there may be mentioned such hydroxy-$C_1$-$C_6$ alkyl groups as hydroxymethyl, 1-hydroxyethyl, 2-hydroxyethyl, 1-methyl-1-hydroxyethyl, 3-hydroxypropyl, 4-hydroxybutyl, 1,1-dimethyl-2-hydroxyethyl, 5-hydroxypentyl and 6-hydroxyhexyl, among others.

As the N,N-di($C_1$–$C_6$ alkyl)aminocarbonyl group, there may be mentioned such N,N-di[$C_1$–$C_6$ alkyl)aminocarbonyl groups as N,N-dimethylamonocarbonyl, N,N-diethylamonocarbonyl, N,N-dipropylaminocarbonyl, N,N-diisopropylaminocarbonyl, N,N-dibutylaminocarbonyl, N,N-di-tert-butylaminocarbonyl, N,N-dipentylaminocarbonyl, N,N-dihexylaminocarbonyl, N-methyl-N-hexylaminocarbonyl and N-ethyl-N-propylaminocarbonyl, among others.

As the $C_1$–$C_6$ alkylene group, there may be mentioned straight or branched $C_1$–$C_6$ alkylene groups such as methylene, ethylene, trimethylene, 1-methylmethylene, tetramethylene, 2-methyltrimethylene, pentamethylene, hexamethylene and the like.

The compounds of the invention, which are represented by the above general formula (1) can be classified more specifically into compounds of the formula (1A) shown below and compounds of the formula (11) also shown below.

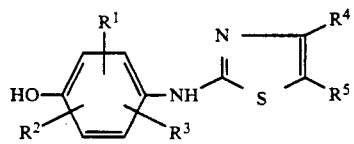
(1A)

In the above formula, $R^1$, $R^2$, $R^3$, $R^4$ and $R^5$ are as defined above, to the exclusion of the combinations wherein $R^3$ is a hydrogen atom, $R^4$ is a $C_1$–$C_6$ alkyl or phenyl group and $R^5$ is a hydrogen atom.

Among the compounds of the above general formula (1A) preferred are those compounds in which one of the above-mentioned groups $R^1$–$R^3$ is a hydrogen atom and the other two are each a tert-butyl group. As particularly preferred compounds of the invention which belong to the class of compounds of the above general formula (1A), there may be mentioned, among others, compounds of the general formula (1A′) shown below.

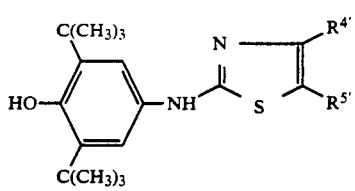
(1A′)

In the above formula (1A′), $R^{4'}$ is a hydrogen atom or a hydroxy-$C_1$–$C_6$ alkyl, $C_1$–$C_6$ alkyl or carbazoyl group and $R^{5'}$ is a hydrogen atom or a $C_1$–$C_6$ alkoxy-carbonyl, $C_1$–$C_6$ alkylthio or $C_1$–$C_6$ alkyl group.

The following are typical examples among the preferred compounds of the above general formula (1A′):

2,6-Di-tert-butyl-4-[(2-thiazolyl)amino]phenol,
2,6-Di-tert-butyl-4-[(4-hydroxymethyl-2-thiazolyl)amino]phenol,
2,6-Di-tert-butyl-4-[(4-methyl-5-ethoxycarbonyl-2-thiazolyl)amino]phenol,
2,6-Di-tert-butyl-4-[(4-carbazoyl-2-thiazolyl)amino]phenol,
2,6-Di-tert-butyl-4-[(4-methyl-5-ethylthio-2-thiazolyl)amino]phenol,
2,6-Di-tert-butyl-4-[(4-pentyl-5-methyl-2-thiazolyl)amino]phenol and
2,6-Di-tert-butyl-4-[(4,5-dimethyl-2-thiazolyl)amino]phenol.

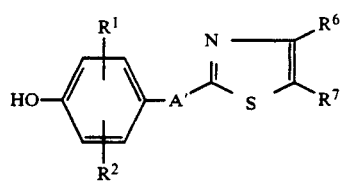
(1B)

In the above formula, $R^1$ and $R^2$ are as defined above, A′ is the same as the group A defined above provided that A′ is other than an imino group, and $R^6$ and $R^7$ are the same or different and each is a hydrogen atom or a $C_1$–$C_6$ alkyl, phenyl, carboxyl, carboxy-$C_1$–$C_6$ alkyl, $C_1$–$C_6$ alkoxycarbonyl-$C_1$–$C_6$ alkyl, $C_1$–$C_6$ alkoxy-carbonyl or hydroxy-$C_1$–$C_6$ alkyl group.

Preferred among the compounds of the above general formula (1B) are those compounds in which the above groups $R^1$ and $R^2$ each is a tert-butyl group. As particularly preferred compounds of the invention which belong to the class of compounds of the above general formula (1B), there may be mentioned, among others, compounds of the following general formula (1B′):

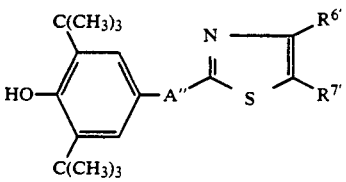
(1B′)

In the above formula, $R^{6'}$ is a hydrogen atom or a $C_1$–$C_6$ alkoxy-carbonyl group, $R^{7'}$ is a hydrogen atom and A″ is an oxygen or sulfur atom.

As examples of the preferred compounds of the above general formula (1B′), there may be mentioned the following compounds:
2,6-Di-tert-butyl-4-[(4-ethoxycarbonyl-2-thiazolyl)oxy]phenol and
2,6-Di-tert-butyl-4-[(2-thiazolyl)thio]phenol.

The compounds of the invention and salts thereof are pharmacologically active. Thus, for instance, they have angiogenesis inhibiting activity, in animals, particularly in mammals. The term "angiogenesis inhibiting" is used herein to refer to inhibition of the formation of new blood vessels which is known to take place excessively or actively under morbid conditions such as growth of tumor, retinopathy and psoriasis or in the process of healing of wounds. Therefore, the compounds of the invention and salts thereof are useful in the treatment of such diseases as malignant tumor, retinopathy and psoriasis.

The compounds of the invention and salts thereof are characterized by long duration of the above-mentioned pharmacological activity, by substantial freedom from such adverse effects as gastric ulceration and renal disorder and by low toxicity. From this viewpoint, too, they are profitable as the drugs mentioned above.

In the following, methods of production of the compounds of the invention are described in detail.

The thiazole derivatives of the invention which are represented by the above general formulas (1A) and (1B) can be produced by several methods which respectively involve the reaction processes given below:

[Reaction process 1]

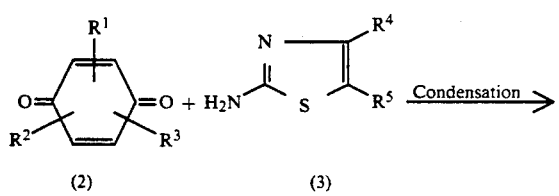

(2)   (3)

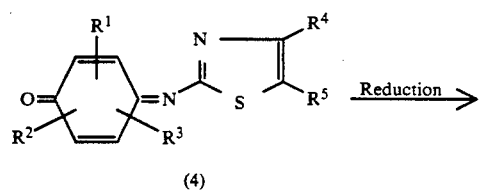

(4)

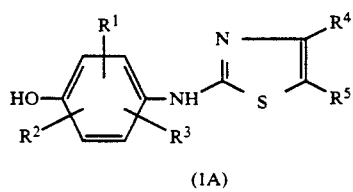

(1A)

In the above formulas, $R^1$, $R^2$, $R^3$, $R^4$ and $R^5$ are as defined above.

According to the reaction process 1, the compounds (1A) of the invention can be obtained by subjecting the quinone derivative (2) and the aminothiazole derivative (3) to condensation reaction, followed by reduction.

The aminothiazole derivative (3) to be used in the above process can be prepared by a known method [cf. J. V. Metzger (editor): The Chemistry of Heterocyclic Compounds, volume 34, 1979, John Wiley & Sons].

The above-mentioned condensation reaction can be carried out essentially by the method of Weingarten et al. as described in J. Org. Chem., 32, 3246 (1967), the method of Figueras et al. as described in J. Org. Chem., 36, 3497 (1971) or the method of Reiker et al. as described in Tetrahedron, 23, 3723 (1967). Thus, said condensation reaction can be effected in the presence of a catalytic amount to an approximately equimolar amount of titanium tetrachloride, boron trifluoride-etherate, acetic acid or the like, in the absence of any solvent or in an appropriate inert organic solvent such as 1,2-dichloroethane, chloroform, benzene, toluene, tetrahydrofuran or dioxane, within the temperature range of room temperature to about 200° C, using about 1–5 moles of the compound (3) per mole of the compound (2), to give the compound (4).

The compound (4) obtained in the above manner can be submitted to the subsequent reduction reaction without isolation thereof from the reaction system. Said compound may of course be isolated, however.

The reduction reaction can be conducted in the conventional manner using, for example, sodium hydrosulfite, sodium borohydride or the combination of zinc and acetic acid, to give the compound (1A) of the invention.

[Reaction process 2]

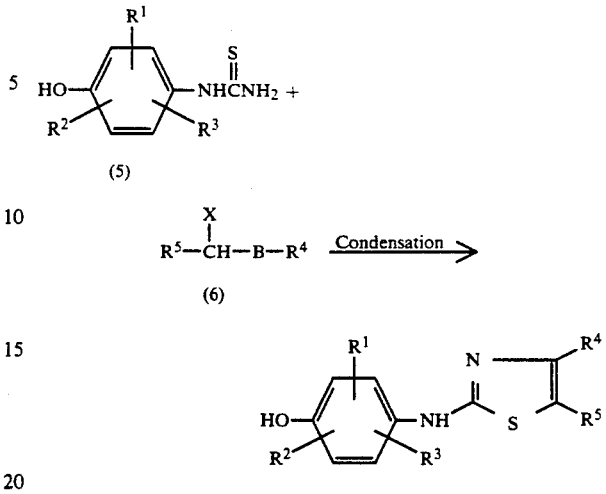

In the above formulas, $R^1$, $R^2$, $R^3$, $R^4$ and $R^5$ are as defined above, X is a halogen atom and B is a carbonyl group, which may optionally be protected.

Referring to the above, as the carbonyl group, which may optionally be protected, there may be mentioned, in addition to the carbonyl group itself, a di-$C_1$–$C_6$alkyl acetal residue, such as the residue of dimethyl acetal, methyl ethyl acetal, diethyl acetal, dipropyl acetal, dibutyl acetal, dipentyl acetal, dihexyl acetal or the like, or a cyclic acetal residue, such as the residue of ethylene acetal, trimethylene acetal, tetramethylene acetal or the like, for instance.

The method illustrated by the reaction process 2 comprises reacting a thiourea derivative of the general formula (5) with a compound of the general formula (6) for thiazole ring formation. The starting compound (5) can be prepared by a known method [cf. Shaulov et al., Neftekhimiya, 21, 467 (1981)].

When B in the compound (6) is a carbonyl group, the above reaction is carried out by causing the compound (5) to act on the compound (6) in an inert organic solvent, such as water, methanol, ethanol, tetrahydrofuran, dioxane or acetic acid, at about 50°–150° C., preferably at about 80°–100° C. The proportions of the compound (5) and the compound (6) are not critical. Desirably, however, the compound (6) is used generally in an amount of about 1–5 moles, preferably about 1–3 moles, per mole of the compound (5). The reaction reaches completion generally in about 10 minutes to about 20 hours.

When B in the compound (6) is a protected carbonyl group, the reaction is recommendably carried out with a catalytic amount of an acid, such as p-toluenesulfonic acid, pyridine hydrochloride, sodium hydrogen sulfate, sulfuric acid, phosphoric acid or polyphosphoric acid, added to the compound (6).

Among the thiazole derivatives of the invention as represented by the general formula (1A), those compounds in which the substituent $R^4$ or $R^5$ on the thiazole ring is a carbazoyl group can be produced by using a compound having an ester residue as the corresponding group (i.e. an ester) as the starting compound and subjecting this to hydrazide formation reaction.

This hydrazide formation reaction can be carried out in the conventional manner by causing a large excess, generally about 50–300 moles per mole of the starting ester compound, of hydrazine hydrate to act on said starting ester compound in an alcohol solvent, such as ethanol, methanol or tert-butanol, under temperature conditions within the temperature range of room temperature to the boiling point of the solvent, for about 5 minutes to about 20 hours.

[Reaction process 3]

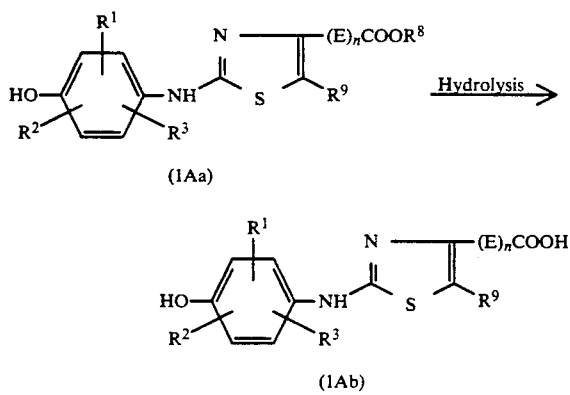

(1Aa)

(1Ab)

In the above formulas, $R^1$, $R^2$ and $R^3$ are as defined above, E is a $C_1-C_6$ alkylene or $C_2-C_6$ alkenyl group, $R^8$ is a $C_1-C_6$ alkyl group, $R^9$ is a hydrogen or halogen atom or a $C_1-C_{20}$ alkyl, phenyl, phenylthio, $C_1-C_6$ alkylthio, $C_1-C_6$ alkylthio-$C_1-C_6$ alkyl, nitro, carboxy-$C_2-C_6$ alkenyl, carbazoyl, carboxyl, piperidinocarbonyl, N,N-di($C_1-C_6$ alkyl)aminocarbonyl, N-phenylaminocarbonyl, carboxy-$C_1-C_6$ alkyl or hydroxy-$C_1-C_6$ alkyl group and n is 0 or 1.

The hydrolysis reaction shown in the above reaction process 3 can be effected by treating the compound (1Aa) with about 2-30 moles, per mole of said compound, of sodium hydroxide, potassium hydroxide or the like in a mixed solvent composed of an appropriate inert organic solvent, such as methanol, ethanol, tetrahydrofuran or dioxane, and water, in the presence of about 2-20 moles, per mole of the compound (1Aa), of a reducing agent, such as sodium hydrosulfite, at a temperature within the range of 0° C. to the boiling point of the solvent, preferably 0° C. to about room temperature.

The above hydrolysis reaction can also be carried out under acidic conditions. This can be effected essentially by the method of E. L. Eliel et al. [Organic Syntheses, IV, 169 (1963)] by treating the compound (1Aa) with a catalytic amount to about 10 moles, per mole of said compound, of an appropriate acid, such as hydrochloric acid or hydrobromic acid, without solvent or in an appropriate solvent, such as acetic acid, at a temperature of room temperature to about 120° C.

Thus the desired compound (1Ab) can be obtained.

[Reaction process 4]

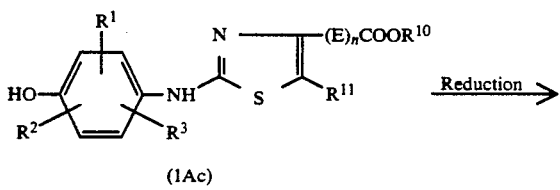

(1Ac)

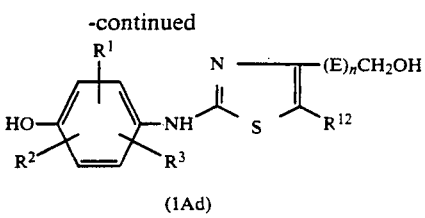

(1Ad)

In the above formulas, $R^1$, $R^2$, $R^3$, E and n are as defined above, $R^{10}$ is a hydrogen atom or a $C_1-C_6$ alkyl group, $R^{11}$ is a hydrogen or halogen atom or a $C_1-C_{20}$ alkyl, phenyl, phenylthio, $C_1-C_6$ alkylthio, $C_1-C_6$ alkylthio-$C_1-C_6$ alkyl, nitro, $C_1-C_6$ alkoxy-carbonyl-$C_1-C_6$ alkyl, carboxyl, carboxy-$C_1-C_6$ alkyl or hydroxy-$C_1-C_6$ alkyl group and $R^{12}$ is a hydrogen or halogen atom or a $C_1-C_{20}$ alkyl, phenyl, phenylthio, $C_1-C_6$ alkylthio, $C_1-C_6$ alkylthio-$C_1-C_6$ alkyl, nitro or hydroxy-$C_1-C_6$ alkyl group.

The compound (1Ad) can be produced from the compound (1Ac) by carrying out the reduction reaction shown in the above reaction process 4.

Said reduction reaction can be performed by using about 1-10 moles, per mole of the compound (1Ac), of an appropriate reducing agent, such as lithium aluminum hydride, aluminum hydride or diborane, in an inert organic solvent, such as diethyl ether or tetrahydrofuran, at a temperature of about 0°-50° C., preferably at about 0° C. to about room temperature, to give the desired compound (1Ad).

[Reaction process 5]

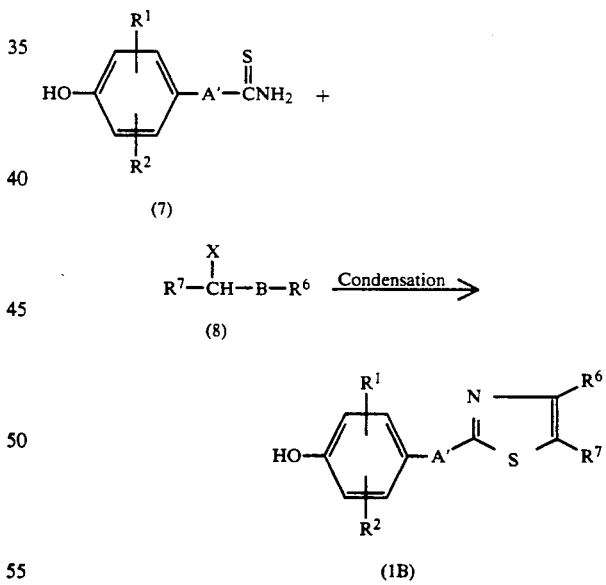

In the above formulas, $R^1$, $R^2$, $R^6$, $R^7$, X, A' and B are as defined above.

According to the method illustrated by the above reaction process 5, there can be produced the desired compounds (1B) of the invention by subjecting the thiocarbamate derivative, dithiocarbamate derivative or thioacetamide derivative of general formula (7) and the haloacetal derivative or halocarbonyl derivative of general formula (8) to condensation reaction for thiazole ring formation. Said condensation reaction can be carried out in the same manner as that shown by the reaction process 2 described above.

Among the starting compounds of general formula (7) to be used in the above process, the thiocarbamate derivative and dithiocarbamate derivative can be prepared, for example by the method of Maeda et al. as described in Chem. Pharm. Bull., 31, 3424 (1983), namely by allowing hydrogen sulfide to add to the corresponding di($C_1$-$C_6$ alkyl)hydroxyphenyl cyanate and di($C_1$-$C_6$ alkyl)hydroxyphenyl thiocyanate, respectively. The thioacetamide derivative can be produced, for example from the corresponding di($C_1$-$C_6$ alkyl)hydroxyphenylacetonitrile by the method of Fairfull et al. as described in J. Chem. Soc., 742 (1952).

The other starting compounds, namely the haloacetal derivative and halocarbonyl derivative of general formula (8) are all known compounds.

[Reaction process 6]

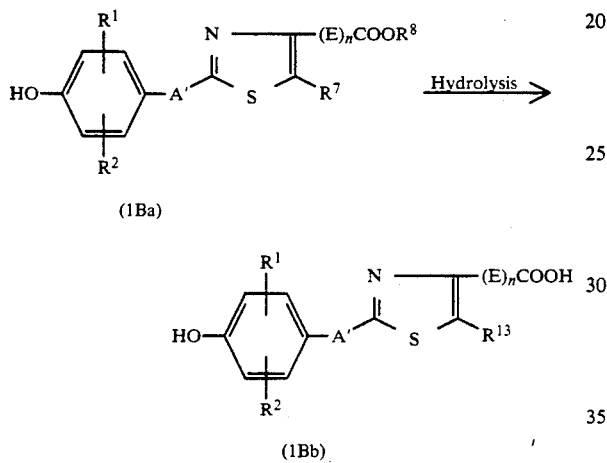

In the above formulas, $R^1$, $R^2$, $R^7$, $R^8$, A', E and n are as defined above and $R^{13}$ is a hydrogen atom or a $C_1$-$C_6$ alkyl, phenyl, carboxy-$C_1$-$C_6$ alkyl, carboxyl or hydroxy-$C_1$-$C_6$ alkyl group.

In accordance with the reaction process 6, the compound (1Bb) can be produced by hydrolysis of the compound (1Ba). The hydrolysis reaction can be effected in the same manner as described above for the reaction process 3.

[Reaction process 7]

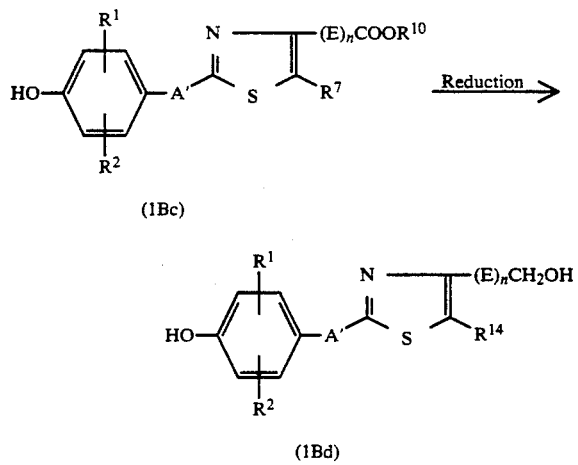

In the above formulas, $R^1$, $R^2$, $R^7$, $R^{10}$, A', E and n are as defined above and $R^{14}$ is a hydrogen atom or a $C_1$-$C_6$ alkyl, phenyl or hydroxy-$C_1$-$C_6$ alkyl group.

According to the reaction process 7, the compound (1Bd) can be obtained by reduction of the compound (1Bc). The reduction reaction can be effected in the same manner as described above for the reaction process 4.

[Reaction process 8]

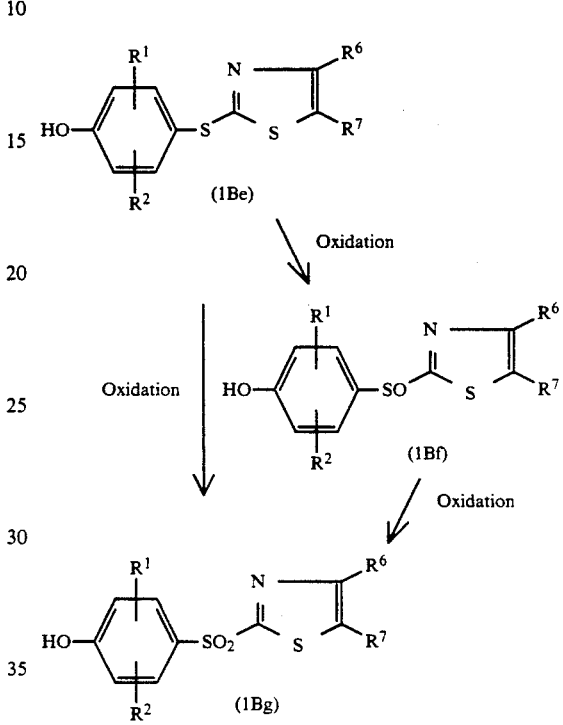

In the above formulas, $R^1$, $R^2$, $R^6$ and $R^7$ are as defined above.

According to the method shown by the above reaction process 8, the sulfinyl compound (1Bf) or sulfonyl compound (1Bg) can be produced by oxidation of the compound (1Be). Said sulfonyl compound (1Bg) can also be produced by oxidation of said sulfinyl compound (1Bf).

Each oxidation reaction can be carried out in an inert organic solvent such as dichloromethane, chloroform, carbon tetrachloride, acetic acid or water, or a mixed solvent composed of these. The production of the compound (1Bf) from the compound (1Be) can be carried out advantageously by using an organic peracid, such as m-chloroperbenzoic acid or peracetic acid, or an inorganic peracid, such as hydrogen peroxide in an equimolar amount relative to the compound (1Be). The production of the compound (1Bg) from the compound (1Bf) can be performed by using an organic peracid such as mentioned above in an amount of about 2-5 moles per mole of the starting compound.

The compounds of the invention as obtained by the reactions shown in the above reaction processes can be isolated and purified with ease by the conventional means of isolation. As examples of said means of isolation, there may be mentioned solvent extraction, recrystallization, column chromatography and so forth.

The thus-obtained compounds of the invention can be easily converted to pharmaceutically acceptable acid addition salts thereof by addition reaction of appropriate acidic compounds in the conventional manner. Said acid addition salts have the same pharmacological activities as the compounds of the invention in the free form have. The present invention includes within the scope thereof such acid addition salts as well. As the acidic compounds capable of forming the above-mentioned acid addition salts, there may be mentioned, among others, such inorganic acids as hydrochloric acid, sulfuric acid, phosphoric acid and hydrobromic acid, and such organic acids as maleic acid, fumaric acid, malic acid, tartaric acid, citric acid, benzoic acid and benzenesulfonic acid. Furthermore, among the compounds of the invention, those having a free carboxyl group can be easily converted to pharmaceutically acceptable salts thereof, such as alkali metal salts (e.g. sodium salt, potassium salt), calcium salt and magnesium salt in the conventional manner. The thus-obtained metal salts also have the same pharmacological activities as the above-mentioned acid addition salts and the compounds of the invention in the free form have. The present invention thus also includes such salts.

The compounds of the invention are generally used in the form of ordinary pharmaceutical preparations. The preparations are prepared by using fillers, extenders, binders, humectants, disintegrating agents, surfactants, lubricants and other diluents or excipients which are in ordinary use. As said pharmaceutical preparations, various forms can be selected depending on the therapeutic purposes. As typical examples, there may be mentioned tablets, pills, powders, solutions, suspensions, emulsions, granules, capsules, suppositories, injections (solutions, suspensions, etc.) and ointments, among others. In forming tablets, use can be made of carriers, for example excipients such as lactose, saccharose, sodium chloride, glucose, urea, starch, calcium carbonate, kaolin, crystalline cellulose, silicic acid and the like, binders such as water, ethanol, propanol, simple syrup, glucose solution, starch solution, gelatin solution, carboxymethylcellulose, shellac, methylcellulose, potassium phosphate, polyvinylpyrrolidone and the like, disintegrants such as dried starch, sodium alginate, agar powder, laminaran powder, sodium hydrogen carbonate, calcium carbonate, polyoxyethylenesorbitan fatty acid esters, sodium lauryl sulfate, stearic acid monoglyceride, starch, lactose and the like, disintegration inhibitors such as saccharose, stearin, cacao butter, hydrogenated oils and the like, absorption promoters such as quaternary ammonium salts, sodium lauryl sulfate and the like, humectants such as glycerin, starch and the like, adsorbents such as starch, lactose, kaolin, bentonite, colloidal silicic acid and the like, and lubricants such as purified talc, stearic acid salts, boric acid powder, polyethylene glycol and the like. Furthermore, the tablets may be converted to tablets provided with ordinary coat layers as necessary, such as sugar-coated tablets, gelatin-encapsulated tablets, enteric coated tablets, film-coated tablets and, furthermore, double- or multi-layer tablets. In forming pills, use can be made of carrier, for example excipients such as glucose, lactose, starch, cacao butter, hardened vegetable oils, kaolin, talc and the like, binders such as gum arabic powder, tragacanth powder, gelatin, ethanol and the like, and disintegrants such as laminaran, agar and the like. In forming suppositories, such carriers can be used as polyethylene glycol, cacao butter, higher alcohols, higher alcohol esters, gelatin, semisynthetic glycerides and the like. Capsules are prepared in the conventional manner generally by mixing the compound of the invention or a salt thereof with various carriers such as mentioned above and filling the mixture into hard gelatin capsules, soft capsules and the like. In preparing injections, solutions, emulsions and suspensions are sterilized and should preferably be isotonic with the blood and, in forming these forms, use can be made of diluents such as water, ethyl alcohol, polyethylene glycol, propylene glycol, ethoxylated isostearyl alcohol, polyoxyisostearyl alcohol, polyoxyethylenesorbitan fatty acid esters and the like. In this case, the pharmaceutical preparations may contain sodium chloride, glucose and/or glycerin in an amount sufficient to render the solutions isotonic, or there may be added an ordinary solubilizing agent, buffer, analgesic and/or the like. If necessary, the pharmaceutical preparations may contain colorants, preservatives, aromas, flavors, sweeteners and the like and/or other drugs. In making up preparations in the form of pastes, creams and gels, use can be made of. diluents such as white petrolatum, paraffin, glycerin, cellulose derivatives, polyethylene glycol, silicones, bentonite and the like.

The quantity of the compounds of the invention to be contained in the pharmaceutical preparations according to the invention is not critical but is selected within a broad range in an appropriate manner. Generally, however, the pharmaceutical preparations should recommendably contain 1-70% by weight of the compounds.

The method of administering the above-mentioned pharmaceutical preparations is not critical but may selected depending on the preparation form, the age, sex and other conditions of the patient, the severity of the disease and other factors. Tablets, pills, solutions, suspensions, emulsions, granules and capsules, for instance, are administered orally. Injections are administered intravenously either alone or in admixture with ordinary nutrient fluid components such as glucose, amino acids and the like, or, as necessary, administered by themselves intramuscularly, intradermally, subcutaneously or intraperitoneally. Suppositories are administered rectally.

The dose of the above-mentioned pharmaceutical preparations is selected depending on the method of administration, the age, sex and other conditions of the patient, the severity of the disease and other factors. Generally, however, the daily dose of the compounds of the invention which are active ingredients should advisably be about 0.5-500 mg per kilogram of body weight. Said preparations can be administered in 1 4 divided doses daily.

EXAMPLES

In the following, some reference examples are given for the production of starting compounds for producing the compounds of the invention, which are followed by examples describing the production of a large number of compounds of the invention.

Reference Example 1

Production of 0-(3,5-di-tert-butyl-4-hydroxyphenyl) thiocarbamate 3,5-Di-tert-butyl-4-hydroxyphenyl cyanate (25.0 g) and 0.7 g of triethylamine were dissolved in 400 ml of diethyl ether, and hydrogen sulfide was blown into the solution at room temperature over 6 hours. Then, the reaction mixture was concentrated, and the crude product thus obtained was washed with hexane to give 25.0 g of the desired compound as a colorless solid.

Melting point : 173°–175° C. $^1$H-NMR (CDCl$_3$) : δ: 1.43 (s, 18H), 5.15 (s, 1H), 6.90 (s, 2H).

Reference Example 2

Production of 3,5-di-tert-butyl-4-hydroxyphenyl dithiocarbamate 3,5-Di-tert-butyl-4-hydroxyphenyl thiocyanate (8.7 g) and 0.3 g of triethylamine were dissolved in 80 ml of diethyl ether, and hydrogen sulfide was blown into the solution at room temperature over 4.5 hours. The reaction mixture was concentrated, and the crude product thus obtained was washed with diethyl ether to give 7.5 g of the desired compound as a colorless solid.

Melting point : 190.5°–191.5° C. $^1$H-NMR (CDCl$_3$) : δ: 1.44 (s, 18H), 5.60 (s, 1H), 6.56 (broad, 1H), 7.32 (s, 2H), 7.88 (broad, 1H).

Reference Example 3

Production of 3,5-di-tert-butyl-4-hydroxyphenyl thioacetamide 3,5-Di-tert-butyl-4-hydroxyphenylacetonitrile (20.0 g) and 11.4 ml of triethylamine were dissolved in 40 ml of pyridine, and hydrogen sulfide was blown into the solution at room temperature over 13 hours. The reaction mixture was concentrated, and the crude product thus obtained was purified by silica gel column chromatography (diethyl ether-hexane =3:7) to give 4.9 g of the desired compound as a colorless solid.

Melting point : 147 –148° C. $^1$H-NMR (CDCl$_3$) : δ: 1.44 (s, 18H), 4.02 (s, 2H), 5.24 (s, 1H), 6.77 (broad, 1H), 7.01 (s, 2H), 7.83 (broad, 1H).

Example 1

Production of 2,6-di-tert-butyl-4-[(5-methyl-2-thiazolyl)amino]phenol 2,6-Di-tert-butyl-1,4-benzoquinone (2.20 g) and 3.43 g of 2-amino-5-methylthiazole were dissolved in 60 ml of anhydrous dichloroethane, 0.55 ml of titanium tetrachloride chloride was added, and the mixture was heated under reflux for 14.5 hours. The mixture was then cooled to room temperature, a solution of 40 g of sodium hydrosulfite in 150 ml of water was added, and the resultant mixture was stirred for 2 hours. The insoluble matter was filtered off, the filtrate was allowed to undergo phase separation, and the aqueous layer was further extracted with dichloromethane. The organic layers were combined, washed with saturated aqueous sodium chloride solution, dried over sodium sulfate and concentrated. Purification of the crude product thus obtained by silica gel column chromatography (diethyl ether-hexane =3:7) gave 1.07 g of the desired compound.

Some physical properties of the compound obtained are shown in Table 1.

Examples 2-8

The compounds specified in Table 1 for Examples 2-8 were produced in the same manner as in Example 1.

Example 9

Production of 2,6-di-tert-butyl-4-[(5-hexyl-2-thiazolyl)amino]phenol 3,5-Di-tert-butyl-4-hydroxyphenylthiourea (2.00 g), 1.81 g of α-bromooctylaldehyde dimethyl acetal and 0.06 g of p-toluenesulfonic acid monohydrate were dissolved in 12 ml of acetic acid, and the solution was heated at 90° C. for 1 hour. The reaction mixture was concentrated, saturated aqueous sodium bicarbonate solution was added, and the resultant mixture was extracted with ethyl acetate. The organic layer was washed with saturated aqueous sodium chloride solution, dried over sodium sulfate and concentrated. Purification of the crude product by silica gel column chromatography (diethyl ether-hexane=1:3) gave 1.56 g of the desired compound.

Some physical properties of the compound obtained are shown in Table 1.

Examples 10-14

The compounds specified in Table 1 for Examples 10-14 were produced in the same manner as in Example 9.

Example 15

Production of 2,6-di-tert-butyl-4-[(4-ethoxycarbonyl-2thiazolyl)amino]phenol 3,5-Di-tert-butyl-4-hydroxyphenylthiourea (2.60 g) and 2.01 g of ethyl bromopyruvate were dissolved in 100 ml of ethanol, and the solution was heated under reflux for 3 hours. After addition of water, the reaction mixture was extracted with chloroform. The organic layer was washed with saturated aqueous sodium bicarbonate solution and then with saturated aqueous sodium chloride solution, then dried over magnesium sulfate, and concentrated. Purification of the crude product by silica gel column chromatography (chloroform-ethyl acetate=15:1) gave 1.80 g of the desired compound.

Some physical properties of the compound obtained are shown in Table 2.

Examples 16-23

The compounds specified in Table 2 for Examples 16-23 were produced in the same manner as in Example 15.

Example 24

Production of 2,6-di-tert-butyl-4-[(4-carboxymethyl-2thiazolyl)amino]phenol 2,6-Di-tert-butyl-4-[(4-ethoxycarbonylmethyl-2-thiazolyl)amino]phenol (produced in Example 17) (0.80 g) was dissolved in 30 ml of ethanol, a solution of 2 g of sodium hydrosulfite in 20 ml of water was added and then 15 ml of 2 N aqueous sodium hydroxide was added, and the resultant mixture was stirred at room temperature for 4 hours. The reaction mixture was cooled in an ice bath and, after addition of 15 ml of 2 N hydrochloric acid and further addition of 3 ml of acetic acid, extracted with dichloromethane. The organic layer was washed with saturated aqueous sodium chloride solution, dried over magnesium sulfate and concentrated. The colorless crystals thus obtained were washed with diethyl ether to give 0.50 g of the desired compound.

Some physical properties of the compound obtained are shown in Table 2.

Example 25

Production of 2,6-di-tert-butyl-4-[(4-hydroxymethyl-2-thiazolyl)amino]phenol dihydrochloride Lithium aluminum hydride (1.37 g) was suspended in 121 ml of diethyl ether and, with ice cooling and stirring, a solution (45 ml) of 1.80 g of 2,6-di-tert-butyl-4-[(4-ethoxycarbonyl-2-thiazolyl)amino]phenol (produced in Example 15) in tetrahydrofuran was added to the suspension. The resultant mixture was further stirred at room temperature for 1.5 hours. Then, with cooling in an ice bath, water and then magnesium sulfate were added and the resultant mixture was stirred for 15 minutes. The insoluble matter was filtered off, and the filtrate was concentrated. The crude product was purified by silica gel (Mallinckrodt) chromatography (chloroform-ethyl acetate=30:1) and then treated with 4 N hydrogen chloride solution in ethyl acetate to give 1.00 g of the desired compound.

Some physical properties of the compound obtained are shown in Table 2.

Examples 26-28

The compounds specified in Table 2 for Examples 26-28 were produced in the same manner as in Example 25.

Example 29

Production of 4-(2-thiazolylamino]-2,3,6-trimethylphenol

Pyridine (3.24 ml) was dissolved in 120 ml of dichloroethane, followed by addition of 1.10 ml of titanium tetrachloride. The mixture was heated under reflux for 15 minutes. Then, 3.00 g of 2,3,5-trimethyl-1,4-benzoquinone and 2.00 g of 2-aminothiazole were added, and the resultant mixture was heated under reflux for 2 hours. The reaction mixture was cooled to room temperature and filtered through a Celite pad, and the insoluble matter was washed with chloroform. The filtrate was concentrated, and the crude product obtained was purified by silica gel column chromatography (diethyl ether-hexane =1:19 1:4) to give 0.70 g of 4-(2-thiazolylimino)-2,3,6-trimethylphenol as a pale red solid melting at 95°-96° C.

4-(2-Thiazolylimino)-2,3,6-trimethylphenol (0.60 g) was dissolved in 10 ml of tetrahydrofuran. To the solution was added a solution of 7.6 g of sodium hydrosulfite in 29 ml of water. The mixture was stirred at room temperature for 45 minutes and then extracted with ethyl acetate. The organic layer was washed with saturated aqueous sodium chloride solution, dried over magnesium sulfate and concentrated. Recrystallization of the crude product obtained from acetonitrile gave 0.56 g of the desired compound as colorless crystals.

Some physical properties of the compound obtained are shown in Table 3.

Example 30

Production of 2-tert-butyl-4-(2-thiazolylamino)-5,6,7,8-tetrahydronaphthol

Pyridine (3.71 ml) was dissolved in 137 ml of dichloroethane, followed by addition of 1.26 ml of titanium tetrachloride. The mixture was heated under reflux for 15 minutes. Then, 5.00 g of 2-tert-butyl-5,6,7,8-tetrahydro-1,4-naphthoquinone and 2.29 g of 2-aminothiazole were added, and the mixture was heated under reflux for 2 hours. The reaction mixture was cooled to room temperature and filtered through Celite pad. The insoluble matter was washed with ethyl acetate. The filtrate was concentrated, and the crude product thus obtained was dissolved in 49 ml of tetrahydrofuran. To the solution was added a solution of 38.9 g of sodium hydrosulfite in 145 ml of water, and the mixture was stirred at room temperature for 15 minutes and then extracted with ethyl acetate. The organic layer was washed with saturated aqueous sodium chloride solution, dried over magnesium sulfate and concentrated. The thus-obtained crude product was purified by silica gel column chromatography (diethyl ether-hexane =2:3) and washed with isopropyl ether to give 0.86 g of the desired compound as a colorless solid.

Some physical properties of the compound obtained are shown in Table 3.

Examples 31-34

The compounds Examples 31-34 were produced in the same manner as in Example 30. The results obtained are shown in Table 3.

Example 35

Production of 2,6-di-di-tert-butyl-4-[(4-carbazoyl-2-thiazolyl)amino]-phenol 2,6-Di-tert-butyl-4-[(4-ethoxycarbonyl-2-thiazolyl)amino]phenol (produced in Example 15) (1.00 g) and 15 ml of 90% hydrazine hydrate were dissolved in 15 ml of ethanol, and the solution was heated at 100° C. for 10 minutes. After cooling to room temperature, the reaction mixture was diluted with water, and the resultant solid was collected by filtration and dried. Recrystallization of the thus-obtained crude product from ethanol gave 0.80 g of the desired compound as colorless crystals.

Some physical properties of the compound are shown in Table 3.

Example 36

Production of 3-[2-(4-hydroxy-3,5-di-tert-butylphenylamino(-4-thiazolyl]-2-propenoic acid hydrochloride A mixture of 1.0 g of methyl 3-[2-(4-hydroxy-3,5-di-tert-butylphenylamino)-4-thiazolyl]-2-propenoate (produced in Example 34), 2.8 ml of 36% hydrochloric acid and 5.6 ml of acetic acid was heated at 50° C. for 17.5 hours. The reaction mixture was concentrated under reduced pressure, the crude product obtained was purified by silica gel column chromatography (chloroform→chloroform-methanol =19:1), the pale red solid obtained was suspended in 40 ml of acetonitrile, 1.3 ml of 4 N hydrogen chloride solution in ethyl acetate was added, and the solid precipitate was collected by filtration. Thus was obtained 0.85 g of the desired compound as a colorless solid.

Some physical properties of the compound are shown in Table 3.

Example 37

Production of 2,6-di-tert-butyl-4-(2-thiazolyloxy)phenol hydrochloride

O-(3,5-Di-tert-butyl-4-hydroxyphenyl) thiocarbamate (1.00 g), 0.66 g of chloroacetaldehyde diethyl acetal and 0.03 g of p-toluenesulfonic acid monohydrate were dissolved in 6 ml of acetic acid, and the solution was heated at 95° C. for 1 hour. The reaction mixture was poured into water and extracted with chloroform. The organic layer was washed with saturated aqueous sodium bicarbonate solution and then with saturated aqueous sodium chloride solution, dried over magnesium sulfate and concentrated. The crude product obtained was dissolved in 10 ml of diethyl ether, 1.1 ml of 4 N hydrogen chloride solution in ethyl acetate was added thereto, and the solid precipitate was collected by filtration and dried to give 0.80 g of the desired compound as a colorless solid.

Some physical properties (melting point and $^1$H-NMR data) of the compound obtained are shown in Table 4.

Example 38

Production of 2,6-di-tert-butyl-4-[(4-methyl-2-thiazolyl)oxy]phenol

O-(3,5-Di-tert-butyl-4-hydroxyphenyl) thiocarbamate (1.5 g) and 1.3 g of chloroacetone were dissolved in 60 ml of acetic acid, and the solution was heated at 90°–100° C. for 15 hours. The reaction mixture was poured into water and extracted with dichloromethane. The organic layer was washed with saturated aqueous sodium bicarbonate solution and then with saturated aqueous sodium chloride solution, dried over magnesium sulfate, and concentrated. The crude product obtained was purified by silica gel column chromatography (diethyl ether-hexane =1:4) to give 1.0 g of the desired compound as a colorless solid.

Some physical properties of the compound obtained are shown in Table 4.

Examples 39–50

The desired compounds were produced from O-(3,5-di-tert-butyl-4-hydroxyphenyl) thiocarbamate, 3,5-di-tert-butyl-4-hydroxyphenyl dithiocarbamate or 3,5-di-tert-butyl-4-hydroxyphenyl thioacetamide on one hand and the corresponding haloacetal derivative or halocarbonyl derivative on the other by following the procedure of Example 37 or 38.

Some physical properties of each of the compounds obtained are shown in Table 4.

Example 51

Production of 2,6-di-tert-butyl-4-[(4-carboxymethyl-2-thiazolyl)oxy]phenol 2,6-Di-tert-butyl-4-[(4-ethoxycarbonylmethyl-2-thiazolyl)oxy]phenol (produced in Example 41) (0.40 g) was dissolved in 15 ml of ethanol, 8 ml of 2 N aqueous sodium hydroxide was added to the solution at room temperature, and the mixture was stirred for 1 hour. The reaction mixture was poured into water and, after acidification to Congo red with 36% hydrochloric acid, extracted with dichloromethane. The organic layer was washed with saturated aqueous sodium chloride solution, dried over magnesium sulfate and concentrated. The crude product obtained was washed with diethyl ether-hexane (1:10) to give 0.30 g of the desired compound as a colorless solid.

Some physical properties of the compound obtained are shown in Table 4.

Examples 52 and 53

The desired compounds were produced from the compounds obtained in Examples 48 and 50, respectively, by following the procedure of Example 51.

Some physical properties of each of the compounds obtained are shown in Table 4.

Example 54

Production of 2,6-di-tert-butyl-4-[(4-hydroxymethyl-2-thiazolyl)oxy]phenol

Lithium aluminum hydride (0.40 g) was suspended in 100 ml of diethyl ether, a solution (30 ml) of 0.80 g of 2,6-di-tert-butyl-4-[(4-ethoxycarbonyl-2-thiazolyl)oxy]phenol (produced in Example 40) in tetrahydrofuran was added to the suspension with stirring at room temperature, and the resultant mixture was stirred for further 4 hours. Water and then magnesium sulfate were added to the reaction mixture with cooling in an ice bath, and the resultant mixture was stirred for 15 minutes. The insoluble matter was filtered off, and the filtrate was concentrated. The crude product obtained was recrystallized from diethyl ether-hexane to give 0.30 g of the desired product as colorless crystals.

Some physical properties of the compound obtained are shown in Table 4.

Examples 55 and 56

The desired compounds were produced from the compounds obtained in Examples 41 and 48, respectively, by following the procedure of Example 54.

Some physical properties of each of the compounds are shown in Table 4.

Example 57

Production of 2,6-di-tert-butyl-4-(2-thiazolylsulfinyl)phenol 2,6-Di-tert-butyl-4-(2-thiazolylthio)phenol (produced in Example 42) (1.60 g) was dissolved in 100 ml of dichloromethane and, with stirring and ice cooling, 1.21 g of 70% m-chloroperbenzoic acid was added, and the mixture was stirred for further 30 minutes. The reaction mixture was washed with saturated aqueous sodium bicarbonate solution and then with saturated aqueous sodium chloride solution, dried over magnesium sulfate and concentrated. Purification of the crude product obtained by silica gel column chromatography (chloroform-ethyl acetate=35:1) gave 1.21 g of the desired product as a colorless solid.

Some physical properties of the compound obtained are shown in Table 4.

Example 58

Production of 2,6-di-tert-butyl-4-(2-thiazolylsulfonyl)phenol 2,6-Di-tert-butyl-4-(2-thiazolylsulfinyl)phenol (produced in Example 57) (0.87 g) was dissolved in 50 ml of dichloromethane and, with ice cooling and stirring, 1.89 g of 70% m-chloroperbenzoic acid was added, and stirring was further continued at room temperature for 30 minutes. The reaction mixture was washed with saturated aqueous sodium bicarbonate solution and then with saturated aqueous sodium chloride solution, dried over magnesium sulfate and concentrated. Purification of the crude product obtained by silica gel column chromatography (chloroform) gave 0.50 g of the desired compound as a colorless solid.

Some physical properties of the compound obtained are shown in Table 4.

TABLE 1

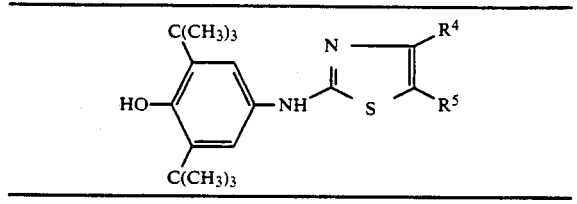

Example 1
$R^4=H$, $R^5=CH_3$
mp 217–218° C.
$^1$H-NMR(CDCl$_3$): δ
1.44(s, 18H), 2.29(d, J=1Hz, 3H)
6.81(d, J=1Hz, 1H), 7.07(s, 2H)
Example 2
$R^4=R^5=H$
mp 167–168° C.
$^1$H-NMR(CDCl$_3$): δ
1.46(s, 18H), 6.49(d, J=4Hz, 1H)
7.15(s, 2H), 7.22(d, J=4Hz, 1H)
Example 3
$R^4=(CH_2)_5CH_3$, $R^5=H$(dihydrochloride)
mp 185–188° C.(decomp.)
$^1$H-NMR(CD$_3$OD): δ
0.91(fused t, 3H), 1.06–1.86(m, 8H)
1.44(s, 18H), 2.61(broad t, J=7Hz, 2H)
6.49(t, J=1Hz, 1H), 7.16(s, 2H)
Example 4
$R^4=(CH_2)_{11}CH_3$, $R^5=H$(dihydrochloride)
mp 60–63° C.(decomp.)
$^1$H-NMR(CD$_3$OD): δ
0.88(fused t, 3H), 1.00–1.88(m, 20H)
1.44(s, 18H), 2.62(broad t, J=7Hz, 2H)
6.51(broad s, 1H), 7.19(broad s, 2H)
Example 5
$R^4=(CH_2)_2CH(CH_3)_2$, $R^5=H$
mp 166–167° C.
$^1$H-NMR(CDCl$_3$): δ
0.89(d, J=6Hz, 6H), 0.95–1.83(m, 3H)
1.43(s, 18H), 2.53(broad t, J=7Hz, 2H)
6.02(t, J=1Hz, 1H), 7.10(s, 2H)
Example 6
$R^4=CH_3$, $R^5=(CH_2)_4CH_3$(dihydrochloride)
mp >135° C.(decomp.)
$^1$H-NMR(CD$_3$OD): δ
0.92(broad t, J=6Hz, 3H)
1.16–1.88(m, 6H), 1.44(s, 18H)
2.20(s, 3H), 2.62(broad t, J=7Hz, 2H)
7.14(s, 2H)
Example 7
$R^4=C_6H_5$, $R^5=(CH_2)_{13}CH_3$(dihydrochloride)
mp 70–75° C.
$^1$H-NMR(CDCl$_3$): δ
0.87(broad t, J=6Hz, 3H)
0.99–1.77(m, 24H), 1.45(s, 18H)
2.73(broad t, J=8Hz, 2H), 7.12(s, 2H)
7.47(broad s, 5H)
Example 8
$R^4=CH_2SCH_3$, $R^5=H$(dihydrochloride)
mp 163–168° C.(decomp.)
$^1$H-NMR(CD$_3$OD): δ
1.45(s, 18H), 2.09(s, 3H)
3.65(s, 2H), 6.74(broad s, 1H)
7.20(s, 2H)
Example 9
$R^4=H$, $R^5=(CH_2)_5CH_3$
mp 144–144.5° C.
$^1$H-NMR(CDCl$_3$): δ
0.87(broad t, J=6Hz, 3H)
1.07–1.87(m, 8H), 1.45(s, 18H)
2.63(broad t, J=7Hz, 2H)
6.83(broad s, 1H), 7.08(s, 2H)
Example 10
$R^4=H$, $R^5=(CH_2)_{11}CH_3$
mp 121–121.5° C.
$^1$H-NMR(CDCl$_3$): δ
0.87(broad t, J=6Hz, 3H)
1.03–1.83(m, 20H), 1.44(s, 18H)
2.63(broad t, J=7Hz, 2H)

TABLE 1-continued

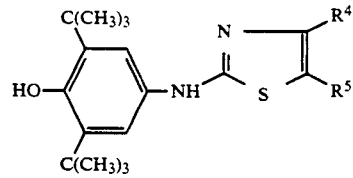

6.82(broad s, 1H), 7.08(s, 2H)
Example 11
$R^4=R^5=CH_3$
mp 234–235° C.(decomp.)
$^1$H-NMR(CDCl$_3$): δ
1.44(s, 18H), 2.13(d, J=1Hz, 3H)
2.19(d, J=1Hz, 3H), 7.07(s, 2H)
Example 12
$R^4=CH_3$, $R^5=SCH_2CH_3$
mp 194–195° C.(decomp.)
$^1$H-NMR(CDCl$_3$): δ
1.22(t, J=8Hz, 3H), 1.45(s, 18H)
2.29(s, 3H), 2.62(q, J=8Hz, 2H)
7.09(s, 2H)
Example 13
$R^4=CH_3$, $R^5=SC_6H_5$
mp 227–228° C.(decomp.)
$^1$H-NMR(CDCl$_3$): δ
1.43(s, 18H), 2.29(s, 3H)
7.00–7.24(m, 7H)
Example 14
$R^4=C_6H_5$, $R^5=SC_6H_5$(dihydrochloride)
mp 182–184° C.
$^1$H-NMR(d$_6$-DMSO): δ
1.40(s, 18H), 7.04–7.52(m, 10H)
7.80–8.00(m, 2H)

TABLE 2

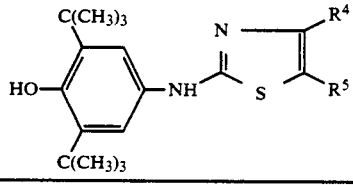

Example 15
$R^4=COOC_2H_5$, $R^5=H$
mp 158.5–160.5° C.
$^1$H-NMR(CDCl$_3$): δ
1.26(t, J=7Hz, 3H), 1.44(s, 18H)
4.22(q, J=7Hz, 2H), 7.12(s, 2H)
7.38(s, 1H)
Example 16
$R^4=H$, $R^5=COOCH_3$
mp 248–248.5° C.
$^1$H-NMR(CDCl$_3$): δ
1.47(s, 18H), 3.82(s, 3H)
7.13(s, 2H), 7.90(s, 1H)
Example 17
$R^4=CH_2COOC_2H_5$, $R^5=H$
mp 160–161.5° C.
$^1$H-NMR(CDCl$_3$): δ
1.26(t, J=7Hz, 3H), 1.44(s, 18H)
3.59(d, J=1Hz, 2H), 4.17(q, J=7Hz, 2H), 6.33(t, J=1Hz, 1H), 7.11(s, 2H)
Example 18
$R^4=CH_3$, $R^5=COOC_2H_5$
mp 230–232° C.(decomp.)
$^1$H-NMR(CD$_3$OD+CDCl$_3$): δ
1.34(t, J=7Hz, 3H), 1.46(s, 18H)
2.54(s, 3H), 4.26(q, J=7Hz, 2H)
7.17(s, 2H)
Example 19
$R^4=COOH$, $R^5=H$(hydrobromide)
mp 255–256° C.(decomp.)
$^1$H-NMR(d$_6$-DMSO): δ
1.39(s, 18H), 7.33(s, 2H)

TABLE 2-continued

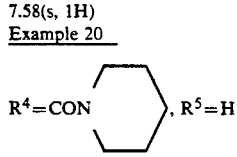

7.58(s, 1H)

Example 20

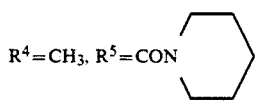

mp 202–202.5° C.(decomp.)
$^1$H-NMR(CDCl$_3$): δ
1.44(s, 18H), 1.42–1.80(m, 6H)
3.50–3.75(m, 4H), 6.91(s, 1H)
7.11(s, 2H)

Example 21
$R^4=CH_3$, $R^5=CON(C_2H_5)_2$
mp 168.5–169° C.(decomp.)
$^1$H-NMR(CDCl$_3$): δ
1.16(t, J=8Hz, 6H), 1.44(s, 18H)
2.24(s, 3H), 3.44(t, J=8Hz, 4H)
7.11(s, 2H)

Example 22

$R^4=CH_3$, $R^5=CON\langle\rangle$ mp 241.5–242.5° C.(decomp.)
$^1$H-NMR(d$_6$-DMSO): δ
1.39(s, 18H), 1.30–1.75(m, 6H)
2.17(s, 3H), 3.30–3.60(m, 4H)
7.29(s, 2H)

Example 23
$R^4=CH_3$, $R^5=CONHC_6H_5$
mp 244–245° C.(decomp.)
$^1$H-NMR(CDCl$_3$): δ
1.45(s, 18H), 2.54(s, 3H)
7.15(s, 2H), 6.96–7.56(m, 5H)

Example 24
$R^4=CH_2COOH$, $R^5=H$
mp 153–154° C.(decomp.)
$^1$H-NMR(CD$_3$OD+CDCl$_3$): δ
1.45(s, 18H), 3.59(broad s, 2H)
6.33(broad s, 1H), 7.15(s, 2H)

Example 25
$R^4=CH_2OH$, $R^5=H$(dihydrochloride)
mp >105° C.(decomp.)
$^1$H-NMR(CD$_3$OD): δ
1.45(s, 18H), 4.50(broad s, 2H)
6.73(broad s, 1H), 7.20(s, 2H)

Example 26
$R^4=H$, $R^5=CH_2OH$(dihydrochloride)
mp >207° C.(decomp.)
$^1$H-NMR(d$_6$-DMSO): δ
1.39(s, 18H), 4.43(broad s, 1H)
4.47(broad s, 1H), 7.16(s, 2H)
7.24(broad s, 1H)

Example 27
$R^4=CH_2CH_2OH$, $R^5=H$(dihydrochloride)
mp 199–200° C.(decomp.)
$^1$H-NMR(d$_6$-DMSO): δ
1.39(s, 18H), 2.70(t, J=6Hz, 2H)
3.65(t, J=6Hz, 2H), 6.59(s, 1H)
7.18(s, 2H)

Example 28
$R^4=CH_3$, $R^5=CH_2OH$(dihydrochloride)
mp >105° C.(decomp.)
$^1$H-NMR(CD$_3$OD): δ
1.44(s, 18H), 2.25(broad s, 3H)

TABLE 2-continued 4.55(broad s, 2H), 7.17(s, 2H)

TABLE 3

Example 29
$R^1=R^2=R^3=CH_3$, $R^4=R^5=H$
mp 212.5–213.5° C.
$^1$H-NMR(d$_6$-DMSO): δ
2.05(s, 3H), 2.12(s, 6H)
6.57(d, J=3.6Hz, 1H), 6.92(s, 1H)
7.04(d, J=3.6Hz, 1H)

Example 30
$R^1=C(CH_3)_3$, $R^2R^3=(CH_2)_4$, $R^4=R^5=H$
mp 191–192° C.
$^1$H-NMR(CDCl$_3$): δ
1.41(s, 9H), 1.73–1.88(m, 4H)
2.58–2.67(m, 4H)
6.47(d, J=3.6H, 1H)
7.17(d, J=3.6Hz, 1H), 7.27(s, 1H)

Example 31
$R^1=R^2=CH(CH_3)_2$, $R^3=R^4=R^5=H$
mp 131.5–132.5° C.
$^1$H-NMR(CDCl$_3$): δ
1.27(d, J=6.8Hz, 12H)
3.19(septet, J=6.8Hz, 2H)
6.52(d, J=3.7Hz, 1H)
7.22(d, J=3.7Hz, 1H), 7.03(s, 2H)

Example 32
$R^1=R^2=C(CH_3)_3$, $R^3=R^4=H$, $R^5=Cl$
mp 198–199° C.(decomp.)
$^1$H-NMR(d$_6$-DMSO): δ
1.38(s, 18H), 6.73(s, 1H)
7.15(s, 1H), 7.29(s, 2H)
9.90(s, 1H)

Example 33
$R^1=R^2=C(CH_3)_3$, $R^3=R^4=H$, $R^5=NO_2$
mp 235–237° C.(decomp.)
$^1$H-NMR(d$_6$-DMSO): δ
1.39(s, 18H), 7.08(s, 1H)
7.30(s, 2H), 8.41(s, 1H)
11.24(s, 1H)

Example 34
$R^1=R^2=C(CH_3)_3$, $R^3=R^5=H$
$R^4=CH=CHCOOCH_3$
mp 210–210.5° C.(decomp.)
$^1$H-NMR(d$_6$-DMSO): δ
1.40(s, 18H), 3.71(s, 3H)
6.47(d, J=15.2Hz, 1H), 6.69(s, 1H)
7.30(s, 1H), 7.43(d, J=15.2Hz, 1H)
7.53(s, 2H), 10.02(s, 1H)

Example 35
$R^1=R^2=C(CH_3)_3$, $R^3=R^5=H$
$R^4=CONHNH_2$
mp 234–235° C.(decomp.)
$^1$H-NMR(d$_6$-DMSO): δ
1.39(s, 18H), 4.50(broad s, 2H)
6.73(s, 1H), 7.35(s, 2H)
7.37(s, 1H), 8.61(s, 1H)
9.93(s, 1H)

Example 36
$R^1=R^2=C(CH_3)_3$, $R^3=R^5=H$

TABLE 3-continued

[Structure: HO-phenyl with R¹, R², R³ substituents, NH-C(=S or similar)-C(R⁴)=C(R⁵)]

$R^4$=CH=CHCOOH (hydrochloride)
mp 230–232° C.(decomp.)
$^1$H-NMR(d$_6$-DMSO): δ
1.40(s, 18H), 6.41(d, J=15.3Hz, 1H)
7.24(s, 1H), 7.34(d, J=15.3Hz, 1H)
7.52(s, 2H), 10.08(broad s, 1H)

TABLE 4

[Structure: 3,5-di-tert-butyl-4-hydroxyphenyl-A-C(=N)-S-C(R⁸)=C(R⁷)]

Example 37
A=O, $R^6$=$R^7$=H (hydrochloride)
mp 155–156° C.(decomp.)
$^1$H-NMR(CD$_3$OD): δ
1.44(s, 18H), 7.22(s, 2H), 7.28(d, J=4.4Hz, 1H), 7.59(d, J=4.4Hz, 1H)

Example 38
A=O, $R^6$=CH$_3$, $R^7$=H
mp 119–120° C.
$^1$H-NMR(CDCl$_3$): δ
1.44(s, 18H), 2.29(d, J=1.1Hz, 3H),
5.16(s, 1H), 6.28(q, J=1.1Hz, 1H),
7.08(s, 2H)

Example 39
A=O, $R^6$=C$_6$H$_5$, $R^7$=H
mp 148–150° C.(decomp.)
$^1$H-NMR(CDCl$_3$): δ
1.46(s, 18H), 5.18(s, 1H), 6.91(s, 1H),
7.17(s, 2H), 7.23–7.51(m, 3H),
7.75–7.91(m, 2H)

Example 40
A=O, $R^6$=COOC$_2$H$_5$, $R^7$=H
mp 110–111° C.
$^1$H-NMR(CDCl$_3$): δ
1.39(t, J=7.0Hz, 3H), 1.44(s, 18H),
4.38(q, J=7.0Hz, 2H), 5.21(s, 1H),
7.09(s, 2H), 7.63(s, 1H)

Example 41
A=O, $R^6$=CH$_2$COOC$_2$H$_5$, $R^7$=H
mp 104–104.5° C.
$^1$H-NMR(CDCl$_3$): δ
1.28(t, J=7.3Hz, 3H), 1.43(s, 18H),
3.65(broad s, 2H), 4.19(q, J=7.3Hz, 2H),
5.17(s, 1H), 6.59(broad s, 1H),
7.09(s, 2H)

Example 42
A=S, $R^6$=$R^7$=H
mp 138.5–139.5° C.
$^1$H-NMR(CDCl$_3$): δ
1.44(s, 18H), 5.48(s, 1H),
7.06(d, J=3.5Hz, 1H), 7.44(s, 2H),
7.59(d, J=3.5Hz, 1H)

Example 43
A=S, $R^6$=CH$_3$, $R^7$=H
mp 118–120° C.
$^1$H-NMR(CDCl$_3$): δ
1.43(s, 18H), 2.37(d, J=0.9Hz, 3H),
5.44(s, 1H), 6.61(fused d, J=0.9Hz, 1H),
7.43(s, 2H)

Example 44
A=S, $R^6$=C(CH$_3$)$_3$, $R^7$=H
mp 139.5–140.5° C.
$^1$H-NMR(CDCl$_3$): δ
1.32(s, 9H), 1.44(s, 18H),
5.44(s, 1H), 6.64(s, 1H),

TABLE 4-continued 7.48(s, 2H)

Example 45
A=S, $R^6$=H, $R^7$=(CH$_2$)$_5$CH$_3$ (hydrochloride)
mp 85–89.5° C.(decomp.)
$^1$H-NMR(CD$_3$OD): δ
0.88(broad t, J=7.0Hz, 3H),
1.08–1.88(m, 8H), 1.45(s, 18H),
2.79(broad t, J=7.5Hz, 2H), 7.53(s, 2H),
7.79(broad s, 1H)

Example 46
A=S, $R^6$=$R^7$=CH$_3$
mp 151–152° C.
$^1$H-NMR(CDCl$_3$): δ
1.44(s, 18H), 2.22(fused d, J=0.7Hz, 3H),
2.26(fused d, J=0.7Hz, 3H), 5.43(s, 1H),
7.45(s, 2H)

Example 47
A=S, $R^6$=C$_6$H$_5$, $R^7$=H
mp 163–164.5° C.
$^1$H-NMR(CDCl$_3$): δ
1.45(s, 18H), 5.47(s, 1H),
7.20(s, 1H), 7.12–7.52(m, 3H),
7.49(s, 2H), 7.72–7.88(m, 2H)

Example 48
A=S, $R^6$=COOC$_2$H$_5$, $R^7$=H
mp 105–108° C.
$^1$H-NMR(CDCl$_3$): δ
1.39(t, J=7.0Hz, 3H), 1.45(s, 18H),
4.40(q, J=7.0Hz, 2H), 5.53(s, 1H),
7.47(s, 2H), 7.90(s, 1H)

Example 49
A=CH$_2$, $R^6$=CH$_3$, $R^7$=H
mp 97.5–98° C.
$^1$H-NMR(CDCl$_3$): δ
1.43(s, 18H), 2.42(d, J=1H:, 3H),
4.19(s, 2H), 5.12(s, 1H),
6.69(fused d, J=1Hz, 1H), 7.10(s, 2H)

Example 50
A=CH$_2$, $R^6$=CH$_2$COOC$_2$H$_5$, $R^7$=H
mp 87–88° C.
$^1$H-NMR(CDCl$_3$): δ
1.27(t, J=8Hz, 3H), 1.43(s, 18H),
3.79(d, J=1Hz, 2H),
4.18(q, J=8Hz, 2H),
4.20(s, 2H), 5.13(s, 1H),
7.01(t, J=1Hz, 1H), 7.09(s, 2H)

Example 51
A=O, $R^6$=CH$_2$COOH, $R^7$=H
mp 176.5–177° C.(decomp.)
$^1$H-NMR(CDCl$_3$): δ
1.43(s, 18H), 3.70(s, 2H)
5.21(broad s, 1H), 6.58(s, 1H),
6.72(broad s, 1H), 7.08(s, 2H)

Example 52
A=S, $R^6$=COOH, $R^7$=H
mp 215–217° C.
$^1$H-NMR(CDCl$_3$+CD$_3$OD): δ
1.46(s, 18H), 7.48(s, 2H),
7.94(s, 1H)

Example 53
A=CH$_2$, $R^6$=CH$_2$COOH, $R^7$=H
mp 153–155° C.(decomp.)
$^1$H-NMR(CDCl$_3$): δ
1.43(s, 18H), 3.84(s, 2H), 4.22(s, 2H),
6.99(s, 1H), 7.08(s, 2H)

Example 54
A=O, $R^6$=CH$_2$OH, $R^7$=H
mp 156–158° C.
$^1$H-NMR(CDCl$_3$): δ
1.44(s, 18H), 4.57(s, 2H), 5.18(s, 1H),
6.60(s, 1H), 7.08(s, 2H)

Example 55
A=O, $R^6$=CH$_2$CH$_2$OH, $R^7$=H

TABLE 4-continued

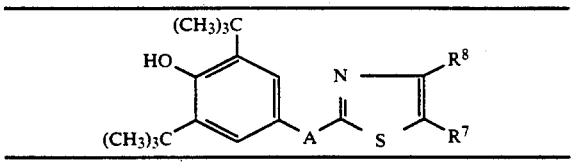

mp 163-164° C.
$^1$H-NMR(CDCl$_3$): δ
1.44(s, 18H), 2.73-3.01(m, 2H),
3.77-4.01(m, 2H), 5.18(s, 1H),
6.40(broad s, 1H), 7.09(s, 2H)

Example 56
A=S, R$^6$=CH$_2$OH, R$^7$=H
mp 206-208° C.
$^1$H-NMR(CDCl$_3$+CD$_3$OD): δ
1.44(s, 18H), 4.63(d, J=0.9Hz, 2H),
7.03(t, J=0.9Hz, 1H), 7.45(s, 2H)

Example 57
A=SO, R$^6$=R$^7$=H
mp 111.5-113.5° C.
$^1$H-NMR(CDCl$_3$): δ
1.42(s, 18H), 5.62(s, 1H),
7.54(d, J=3.1Hz, 1H), 7.55(s, 2H),
7.83(d, J=3.1Hz, 1H)

Example 58
A=SO$_2$, R$^6$=R$^7$=H
mp 173-176° C.
$^1$H-NMR(CDCl$_3$): δ
1.45(s, 18H), 5.84(s, 1H),
7.58(d, J=3.1Hz, 1H), 7.85(s, 2H),
7.90(d, J=3.1Hz, 1H)

In the following, some dosage form examples in which the thiazole derivatives of the invention are used are given and then a pharmacological test made on the compounds of the invention is given by way of example.

| Dosage Form Example 1 | |
|---|---|
| Compound obtained in Example 2 | 200 mg |
| Glucose | 250 mg |
| Distilled water for injection | q.s. |
| Total | 5 ml |

The compound of the invention as obtained in Example 2 and glucose were dissolved in distilled water for injection, and the solution was distributed into 5 ml ampules and, after nitrogen substitution, heat-sterilized to give an injectable preparation according to the above formulation.

| Dosage Form Example 2 | |
|---|---|
| Compound obtained in Example 40 | 100 g |
| Crystalline cellulose (trademark: AVICEL PH101; Asahi Chemical Industry Co., Ltd.) | 40 g |
| Corn starch | 30 g |
| Magnesium stearate | 2 g |
| Total | 172 g |
| Hydroxypropylmethylcellulose (trademark: TC-5; Shin-Etsu Chemical Co., Ltd.) | 10 g |
| Polyethylene glycol 6000 | 3 g |
| Pigment | 0.3 g |
| Titanium dioxide | 0.2 g |
| Water | 86.5 g |
| Total | 100 g |

The compound obtained in Example 40, crystalline cellulose, corn starch and magnesium stearate were weighed according to the above formulation, mixed, and formed into tablets by tableting using sugar-coated punch having a radius of 10 mm. The tablets obtained were coated with a film coating composition composed of the above-mentioned TC-5, polyethylene glycol 6000, pigment, titanium dioxide and water to give film-coated tablets.

| Dosage Form Example 3 | |
|---|---|
| Compound obtained in Example 25 | 2 g |
| Purified lanolin | 5 g |
| White beeswax | 5 g |
| White petrolatum | 88 g |
| Total | 100 g |

An ointment was prepared according to the above formulation by liquefying white beeswax by warming, adding the compound obtained in Example 25, purified lanolin and white petrolatum to the liquefied beeswax, warming the mixture until it became liquefied, and the stirring the mixture until it began to solidify.

Pharmacological Test Example I

"Angiogenesis inhibiting activity test"

(1) Preparation of fetal bovine heart-derived endothelial cells (FBHE cells)

For use in this test, FBHE cells purchased from the ATCC were maintained by subculturing in a medium prepared by adding 20 ng/ml of fibroblast growth factor (FGF; Collaborative Research) to Dulbecco's modified Eagle's medium (DME; Nissui Seiyaku) supplemented with 10% fetal bovine serum (FBS).

From two days before the start of the experiment, the addition of FGF was omitted and FBHE cells were cultured in DME with 10% FBS alone added. At the start of the experiment, the culture medium was removed, phosphate-buffered saline solution (PBS$^{(-)}$; Nissui Seiyaku) was added instead, and cells were rinsed lightly. Then the PBS$^{(-)}$ was removed, an adequate amount of 0.1% EDTA-0.2% trypsin solution was added and, after light rinsing, removed, and cells were stripped off. After addition of 10% FBS-added DME and sufficient pipetting, the cells stripped off were transferred to a centrifugal tube and centrifuged for washing (1,200 rpm, 5 minutes).

The viable cell count was determined using a hemocytometer with the number of dead cells stained with trypan blue being substracted. The cell concentration was adjusted to $3 \times 10^3$ cells/well using 10% FBS-added DME. A cell suspension was thus prepared.

(2) Preparation of test substances

Since the compounds tested were all hardly soluble in water, they were dissolved in dimethyl sulfoxide (DMSO) and the solutions were then diluted with 10% FBS-added DME so as to make the final DMSO concentration 0.05%.

For attaining test substance concentrations, serial double dilution was performed starting with 10 μg/ml.

(3) Procedure for the experiment

The following procedure was followed. Thus, to each well of 96-well Multiplates (Corning), there was added 50 μl of DME containing 10% FBS. Then, 50 μl of each test substance solution having the highest final concentration of 10 μg/ml was added to the well for the highest concentration and then serial dilution was carried out on each plate. Furthermore, 50 μl of FGF (5 ng/ml at maximum) was added to each well, followed by final addition of 100 μl of the cell suspension. The plates prepared by the above procedure were incubated in a carbon dioxide gas incubator for 3 days.

After 3 days of incubation, neutral red was added to each well and the cells were allowed to take up the dye by 2 hours incubation in a carbon dioxide gas incubator. Thereafter, the cells were rinsed twice with PBS$^{(-)}$ or physiological saline. Finally, 100 μl of acid alcohol (a 1:1 mixed solution prepared from 0.1 M aqueous monosodium phosphate solution and ethanol) was added to each well for dissolution thereinto of the dye taken up, and the absorbance of the resultant dye solution was determined using an absorptiometer.

(4) Efficacy evaluation and IC$_{50}$ value determination

The absorbance values measured by the above procedure (3) for each dilution of each test substance with addition of FGF and without addition of FGF (normal condition) were plotted on a graph paper, and the test substance concentration required for 50% inhibition of the proliferation of cultured FBHE cells was determined from the graph obtained and expressed as an IC$_{50}$ value.

The results obtained are shown below in Table 5.

TABLE 5

| Test substance | IC$_{50}$ (μg/ml) FGF− | IC$_{50}$ (μg/ml) FGF+ | FGF−/ FGF+ ratio |
|---|---|---|---|
| Compound obtained in Example 2 | 10.7 | 0.89 | 12.0 |
| Compound obtained in Example 40 | 5.72 | 0.74 | 7.7 |
| Compound obtained in Example 25 | 5.76 | 0.92 | 6.3 |
| Compound obtained in Example 18 | 11.92 | 1.92 | 6.2 |
| Compound obtained in Example 35 | 3.66 | 0.61 | 6.0 |
| Compound obtained in Example 42 | 8.71 | 1.85 | 4.7 |
| Compound obtained in Example 12 | 6.53 | 1.55 | 4.2 |
| Compound obtained in Example 6 | 9.21 | 2.18 | 4.2 |
| Compound obtained in Example 11 | 25.94 | 6.14 | 4.2 |

We claim:

1. A thiazole derivative of the formula

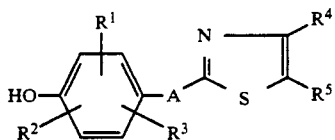

wherein R$^1$ and R$^2$ are the same or different and each is a C$_1$-C$_6$ alkyl group, R$^3$ is a hydrogen atom or a C$_1$-C$_6$ alkyl group, R$^2$ and R$^3$ may combinedly form a —(CH$_2$)$_4$— group, R$^4$ and R$^5$ are the same or different and each is a hydrogen or halogen atom or a C$_1$-C$_{20}$ alkyl, phenyl, phenylthio, C$_1$-C$_6$ alkylthio or C$_1$-C$_6$ alkylthio-C$_1$-C$_6$ alkyl, nitro, C$_1$-C$_6$ alkoxy-carbonyl-C$_2$-C$_6$ alkenyl, carboxy-C$_2$-C$_6$ alkenyl, carbazoyl, carboxyl, carboxy-C$_1$-C$_6$ alkyl, C$_1$-C$_6$ alkoxycarbonyl-C$_1$-C$_6$ alkyl, C$_1$-C$_6$ alkoxy-carbonyl, piperidinocarbonyl, N,N-di(C$_1$-C$_6$ alkyl)-aminocarbonyl, N-phenylaminocarbonyl or hydroxy-C$_1$-C$_6$ alkyl group, and A is an imino group, to the exclusion of the cases where R$^3$ is a hydrogen atom, R$^4$ is a C$_1$-C$_6$ alkyl or phenyl group, R$^5$ is a hydrogen atom and A is an imino group; and salts thereof.

2. A compound and salts thereof as claimed in claim 1, wherein said compound has the general formula

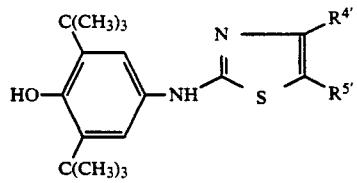

wherein R$^{4'}$ is a hydrogen atom or a hydroxy-C$_1$-C$_6$ alkyl, C$_1$-C$_6$ alkyl or carbazoyl group and R$^{5'}$ is a hydrogen atom or a C$_1$-C$_6$ alkoxy-carbonyl, C$_1$-C$_6$ alkylthio or C$_1$-C$_6$ alkyl group.

3. A compound and salts thereof as claimed in claim 2, wherein said compound is selected from the group consisting of 2,6-di-tert-butyl-4- (2-thiazolyl)amino]phenol, 2,6-di-tert-butyl-4-[(4-hydroxymethyl-2-thiazolyl)amino]phenol, 2,6-di-tert-butyl-4-[(4-methyl-5-ethoxycarbonyl-2-thiazolyl)amino]phenol, 2,6-di-tert-butyl-4-[(4-carbazoyl-2-thiazolyl)amino]phenol, 2,6-di-tert-butyl- 4-[(4-methyl-5-ethylthio-2-thiazolyl)amino]phenol, 2,6-di-tert-butyl-4-[(4-pentyl-5-methyl-2-thiazolyl)amino]phenol and 2,6-di-tert-butyl-4-[(4,5-dimethyl-2-thiazolyl)amino]phenol.

4. A pharmacological composition which contains an amount effective for inhibiting angiogenesis of at least one member of the group consisting of thiazole derivatives of the formula

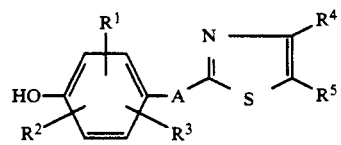

wherein R$^1$, R$^2$, R$^3$, R$^4$, R$^5$ and A are as defined in claim 1, and a salt thereof.

5. A method of inhibiting excessive formation of new blood vessels associated with morbid conditions in a patient by making use of angiogenesis inhibiting activity, which comprises administering to a patient an amount effective for inhibiting angiogenesis of at least one member of the group consisting of thiazole derivatives of the formula

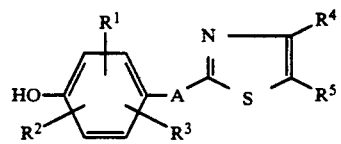

wherein R$^1$, R$^2$, R$^3$, R$^4$, R$^5$ and A are as defined in claim 1, and salts thereof.

* * * * *